United States Patent [19]

Bisagni et al.

[11] Patent Number: 4,465,691
[45] Date of Patent: Aug. 14, 1984

[54] (3,4';4,5)-PYRIDO (3,2-G)-FURO COUMARINS OR (3,4-H) PYRIDO PSORALENS PROCESS OF PREPARATION, APPLICATIONS IN COSMETOLOGY AND IN THERAPEUTICS, AND COSMETOLOGICAL AND PHARMACEUTICAL COMPOSITIONS WITH THEM

[75] Inventors: Emile Bisagni, Orsay; Jacqueline Morin, Gif-Sur-Yvette; Dietrich Averbeck, L'Hay Les Roses; Dubertret Louis, Paris, all of France

[73] Assignee: Institut National de la Sante et de la Recherche Medicale, Paris, France

[21] Appl. No.: 469,454

[22] Filed: Feb. 24, 1983

[30] Foreign Application Priority Data

Feb. 25, 1982 [FR] France .................. 82 03158

[51] Int. Cl.³ ............... C07D 405/12; C07D 491/153; A61K 31/435
[52] U.S. Cl. ..................... 424/256; 546/65; 546/196
[58] Field of Search ............ 546/65; 424/256

[56] References Cited

U.S. PATENT DOCUMENTS 4,260,630 4/1981 Bisagni et al. .............. 424/283

OTHER PUBLICATIONS

Shaikh et al., *Chem. Abstracts*, vol. 92:181047p, (1980), "Benzodipyrans".
*Trends in Photobiology*, Helene et al., eds., Plenum Press, (1982), "Photochemotherapy with Furocoumarins (Psoralens)", pp. 309-320.

Primary Examiner—Donald G. Daus
Assistant Examiner—William A. Teoli, Jr.
Attorney, Agent, or Firm—Oblon, Fisher, Spivak, McClelland & Maier

[57] ABSTRACT

Pyrido (3,4', 4,5) furo (3,2-g) coumarins or pyrido (3,4-h) psoralens having formula I

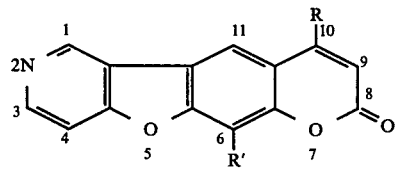

wherein R is a hydrogen radical or a lower alkyl group having from 1 to 4 carbon atoms and R" is a methyl group or a methoxy group. These compounds are photobiologically active and are useful or medicinals and pharmaceutical compositions in association with ultraviolet radiation for treating skin diseases and as cosmetic compositions for skin pigmentation.

12 Claims, No Drawings

(3,4';4,5)-PYRIDO (3,2-G)-FURO COUMARINS OR (3,4-H) PYRIDO PSORALENS PROCESS OF PREPARATION, APPLICATIONS IN COSMETOLOGY AND IN THERAPEUTICS, AND COSMETOLOGICAL AND PHARMACEUTICAL COMPOSITIONS WITH THEM

BACKGROUND OF THE INVENTION

The present invention relates to the field of derivatives of psoralen. It relates more particularly to monofunctional derivatives of psoralen, viz., pyrido (3', 4'; 4,5)furo(3,2-g) coumarins or pyrido(3,4-h) psoralens. The present invention is also concerned with a process of preparing such compounds. The invention also relates to the use of such compounds in cosmetology in particular for stimulating the pigmentation of the skin and as a medicinal for treating skin afflictions. The invention also relates to cosmetic compositions and pharmaceutical compositions having such compounds as their active ingredients.

Photochemical therapy which relies on the activation of photoactive molecules of the furocoumarin family, namely psoralens, on human skin by ultraviolet A radiation is rapidly developing in dermatology. It is indeed a particularly effective and convenient therapeutic technique for the treatment of mild chronic inflammatory dermatoses such as psoriasis which affects 2–3% of the world's population and for the treatment of malignant dermatoses such as mycosis fungoides, malignant cutaneous lymphoma, which is rare but has a particularly severe development. This therapeutic technique has been employed with a certain amount of success in the treatment of numerous chronic inflammatory skin diseases such as atypical eczema, lichen planus, parapsoriasis guttata, pruritis of the hemodialysed beings, in photodermatoses and in depigmentation diseases such as vitiligo.

By way of a reference illustrating the prior art French patent publication No. 2,405,067 may be cited, which concerns pharmaceutical compositions containing monofunctionals derivatives of psoralen for the treatment of skin afflictions. This patent publication, is incorporated by reference in the present specification.

Briefly, for the treatment of skin diseases such as psoriasis, certain furocoumarins or psoralens are administered in association with near ultraviolet light (UVA). This phototherapy is known as PUVA therapy.

The most recent studies have demonstrated that bifunctional psoralens such as 8-methoxy psoralen (abbreviated 8-MOP) and 5-methoxy psoralen (abbreviated 5-MOP) in the conditions of treatment, i.e., in the presence of near ultraviolet light (UVA) is carcinogenic in mice. On the contrary, 3-carbethoxy psoralen (abbreviated 3-CPs) is a monofunctional derivative of psoralen and is completely safe from this point of view. It has also been demonstrated that 3-CPs has a therapeutic activity for patients afflicted with psoriasis.

The psoralens currently used in therapy, such as 8-methoxypsoralen or 5-methoxypsoralen, are capable of forming cross-links in DNA, which cross-links are difficult to repair and capable of introducing errors in genetic replication. This property doubtless explains their high mutagenic activity and carcinogenesis in animals. They are therefore effective medicines but probably not devoid of risk for continual use on human beings. This is the reason photochemical therapy is prohibited for youths up to the age of 18–20 years and one tries to use it as little as possible before the age of 50.

In cosmetology, products are also known which stimulate pigmentation and are comprised of derivatives of psoralen such as 5-methoxy psoralen (or 5-MOP). They have applications in cosmetic compositions for tanning the skin and/or protecting skin against the sun. The drawback with such products is that they are mutagenic.

SUMMARY OF THE INVENTION

The present invention provides novel monofunctional derivatives of psoralen which have properties permitting the improvement of PUVA therapy and stimulation of pigmentation.

Such compounds are useful as medicinals in particular in the field of treatment of skin diseases and more specially for the treatment of benign and malignant inflammatory dermatoses, viz., psoriasis, mycosis fungoides, constitutional and contact dermatites, plaque parapsoriasis and parapsoriasis guttata, alopecias, prurigos, lichen planus pigmentary urticarias as well as pigmentary disorders and phtodermatoses.

The compounds of the invention which have the capacity of stimulating pigmentation of the skin are also useful in the field of cosmetics.

The novel compounds according to the invention are pyrido(3,4-h)psoralens or pyrido(3',4'; 4 ,5)furo(3,2-g)courmarins having the following formula I

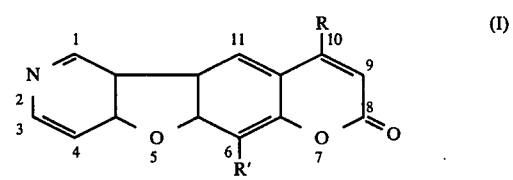

wherein the radical R is a hydrogen atom or a lower alkyl group having from 1 to 4 carbon atoms, and the radical R' is a methyl or methoxy group. Preferably, the radical R is a methyl group or a hydrogen atom.

Considering formula I above, it is noted that the novel derivatives of psoralen according to the invention comprise a substituent R in position 10 which may be a hydrogen atom or a lower alkyl group and a substituent R' in position 6 which may be a methyl ($CH_3$) or methoxy ($OCH_3$) group.

The invention also provides processes for preparing the novel derivatives of formula I.

In a first process of preparation, the starting product is an aminooxy-7-coumarin substituted in position 8 by a methyl or methoxy group and substituted in position 4 by a hydrogen atom or a lower alkyl radical, preferably a methyl radical. Such a starting product may be represented by the following formula II

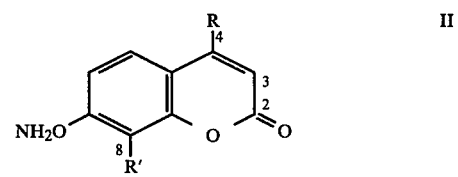

wherein R and R' have the above-mentioned meaning.

The starting product of formula II may be prepared in accordance with the technique described by Dean R.

Bender et al. "Psoralen Synthesis. Improvements in Furano Ring Formation. Application to the synthesis of 4,5'-trimethyl-psoralen", Journal of Organic Chemistry, 44, 2176 (1979). In its application to the present invention this technique is followed by first preparing the appropriate hydroxycoumarin starting with the corresponding phenol, according to a reaction known as the Von Pechmann synthesis. It is a condensation reaction known to those skilled in the art (see Organic Reactions, vol.7, p.1).

The Von Pechmann reaction is used for the synthesis of the coumarins and involves the condensation of a keto ester with a phenol, in particular a polyphenol or an acetate of such a phenol. The reaction is carried out in an acid medium. According to the Bender et al technique, the hydroxycoumarin obtained after the Von Pechmann reaction is reacted with sodium hydride in the dimethylformamide, then with O-2,4-dinitrophenyl-hydroxylamine. This yields the starting product of formula II.

The first step of the process according to the invention comprises reacting product (II) with a 4-piperidone having the formula III

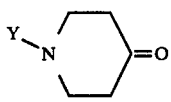

wherein the substituent Y may be a hydrogen atom, a methyl radical or a benzyl group. This reaction is advantageously carried out at normal temperature and at normal pressure in an acidified alcoholic medium. The preferred medium is ethanol containing hydrochloric acid. In this case the hydrochloride obtained precipitates and may be easily isolated by the usual means. An intermediate is obtained which is an oxime having formula IV

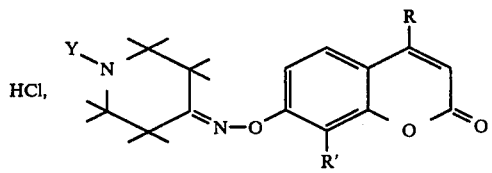

wherein R, R' and Y having the same meaning as indicated above.

The second step of the process of the invention comprises cyclization of the oxime of formula IV. To this end the oxime IV is put into solution in a strong acid medium, preferably acetic acid containing hydrochloric acid, advantageous in the form of dry HCl gas. The most preferred medium is acetic acid containing about 6% dry HCl gas. The reaction is carried out hot, i.e., between about 70° C. and about 90° C., preferably about 80° C.

The second step yield is an intermediate having formula V

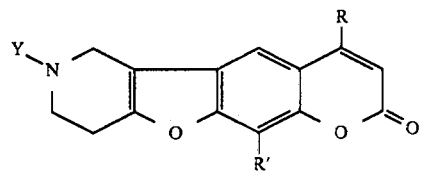

wherein R, R' and Y have the same meaning as indicated above. Product V is a tetrahydro-1,2,3,4-pyrido(3,4-h) psoralen or tetrahydro-1,2,3,4-pyrido(3',4'; 4,5)furo(3,2-g)courmarin. The hydrochloride of compound V is obtained in precipitate form with a yield of 60-75%. This precipitate is therefore easily isolated by the usual techniques. By-products of the reaction are in the mother liquors but are not directly concerned with the invention.

The third and last step of the process according to the invention comprises an aromatization reaction starting with the above intermediate product (V). This reaction is performed in a solvent medium in the presence of a highly active dehydrogenation agent, preferably palladium carbon, for example at 10%. The preferred solvent is Decalin. One operates at the boiling point, that is to say, under reflux with the solvent. Instead of Decalin, any other solvent may be used which is capable of carrying out its function at the reflux temperature and is inert in respect to the reagents present. An example of such a solvent is diphenylether. In the course of the aromatization reaction the group Y, protector of the nitrogen atom, is eliminated and the desired derivative of psoralen of formula (I) is obtained.

The process which has just been described in detail above is suitable for the preparation of all the novel compounds of formula I.

According to the invention another process has been developed which, as an alternative, may be used for preparing compounds of formula I wherein R is a hydrogen atom and R' is a methyl radical or a methoxy radical. This process starts from monomethylic ether of methyl-2- or methoxy-2 resorcin of formula VI

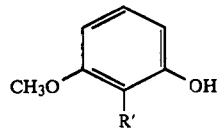

wherein R' is $CH_3$ or $OCH_3$. The starting compound of formula VI where R' is $CH_3$ is obtained from methyl-2 resorcin which is commercially available and the starting compound of formula VI where R is $OCH_3$ is described by Beilstein, vol.6 p.1081.

The other starting product is nitro-3-chloro-4 pyridine of formula VII

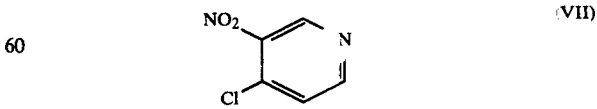

The compound of formula VII may be prepared by known means, for example, as described by R. R. Bishop et al, J. Chem. Soc. (1952), p.437.

The first step of the alternative process according to the invention comprises reacting compounds VI and VII. In general, first of all the alkaline salt of phenol of formula VI is prepared and condensed with nitro-3-chloro-4 pyridine. The reaction is carried out in a solvent such as dimethylformamide, heating at the end of the reaction to complete the same. An intermediate nitrogenous compound is obtained having formula VIII

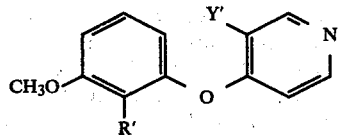
(VIII)

wherein R' is CH₃ or OCH₃ and Y' is NO₂.

The intermediate product VIII wherein Y' is NO₂ is transformed into the corresponding amine wherein Y' is NH₂ by catalytic reduction, i.e., by treatment with hydrogen in the presence of Raney nickel or palladium carbon. The amine of formula VIII in which Y' is NH₂ is then converted in diazo compound in a hydrochloric medium by sodium nitrite to yield a diazo compound,- which does not have to be isolated and is treated immediately. To this end the diazo compound corresponding to formula VIII wherein Y' represents the N₂⁺Cl⁻ radical is cyclized in the presence of a cupric salt (cupric chloride for example) according to the Merwein reaction (Organic Reactions 11, p.189).

Thus, by way of an intermediate product, a compound is obtained having the following formula IX

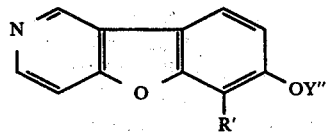
(IX)

wherein Y" represents CH₃ and R' has the same meaning as above, i.e., CH₃ or OCH₃. This product is then subjected to a demethylation reaction, in particular with boiling pyridinium chloride, yielding the compound of formula IX wherein Y" is a hydrogen atom. A hydroxypyridobenzofuran or formula IX is obtained wherein Y" is H. The latter compound is then subjected to a formylation reaction with the aid of hexamethylenetetramine in acetic acid, followed by hydrolysis. An intermediate product is thus obtained having formula X

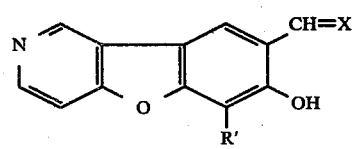
(X)

wherein X represents oxygen and R' is a methyl or methoxy radical.

The aldehyde of formula X is then condensed with diethylmalonate in an alcohol such as ethanol in the presence of a base, preferably piperidine.

A carbethoxypyrido-psoralene is thus obtained having formula XI

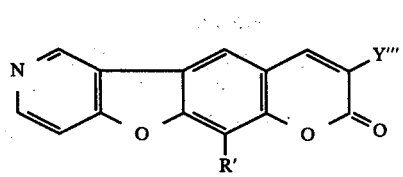
(XI)

wherein Y'''' represents the COOC₂H₅ radical and R' is CH₃ or OCH₃. This product is then hydrolyzed which yields the corresponding acid of formula XI wherein Y'''' is COOH. The hydrolysis is carried out in an acid medium.

A conventional decarboxylation reaction yields pyridospsoralen of formula I wherein R is H and R' is CH₃ or OCH₃.

This alternative process of preparation according to the invention is illustrated by the following reactional diagram for the particular case in which R is H and R' is CH₃.

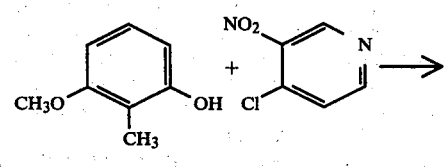

compound 6     compound 7

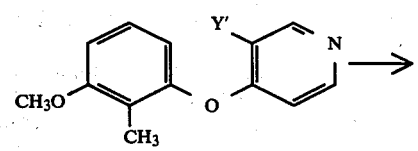

compounds 8a Y' = NO₂
8b Y' = NH₂
8c Y' = N₂⁺Cl⁻

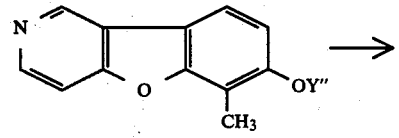

compounds 9a Y" = CH₃
9b Y" = H

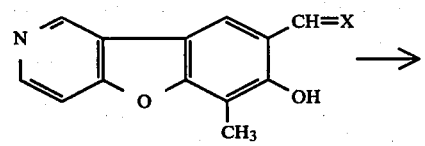

compound 10a X = O

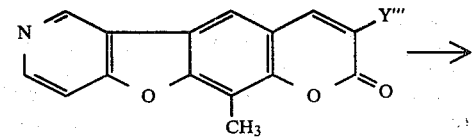

compounds 11a Y'''' = COOC₂H₅
11b Y'''' = COOH

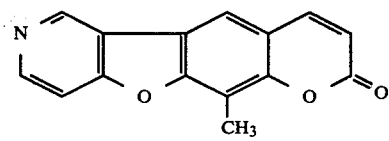

The particular compounds of the above reactional diagram which bear references 6, 7, 8a, 8b, 8c, 9a, 9b, 10a, 11a, and 11b are characterized in the following examples.

The novel compounds of formula I according to the invention are useful as pharmaceuticals or medicinals. Some intermediates such as used in the process according to the invention also have a biological activity. Such is the case of the products of formula V. The novel pharmaceuticals or medicinals containing as an active ingredient at least one of the compounds according to the invention are suitable for the treatment of various skin diseases and more specially the treatment of benign and malignant inflammatory dermatoses, viz., psoriasis, mycosis fungoides, constitutional and contact dermatites, plaque parapsoriasis and parapsoriasis guttata, pruritis, prurigos, lichen planus, pigmentary urticarias as well as pigmentary disorders and photodermatoses.

The compounds of the invention which have the property of stimulating the pigmentation of the skin are also useful in the field of cosmetics.

The treatments of skin afflictions with the compounds according to the invention comprises administering, orally or locally, an effective amount of the compound and subjecting the patient to light in the near ultraviolet range (UVA).

It has now been found that for the topical or local application of ointments or solutions containing about 0.1% to about 2% (by weight) of the therapeutically effective compound may be used. Concentrations of about 0.5% to about 2% are preferred.

As excipients for the solutions or ointments according to the invention, excipients may be used which are currently employed and known to those skilled in the art. Examples of such excipients are cited by Schaefer et al in Archiv. of Dermatology (1976) which document is incorporated by reference.

It is also of course possible to incorporate the compounds of the present invention into other compositions, solutions or ointments or add scents, coloring agents, sun filters, preservatives and all other compounds commonly used. It is also possible to combine two or more photostabilizers or photoprotective agents.

For oral administration amounts between 0.5 and 2 mg/kg are preferred.

As mentioned above, the treatment of skin diseases with the compounds of the invention comprises irradiation with light in the near ultraviolet range (UVA) in a spectrum essentially containing wavelengths between 320 and 380 nm. As explained below, the dose of irradiation at each treatment may, from the outset, be from 5 J/cm$^2$ to 10 J/cm$^2$. Nonetheless, doses ranging up to 20 J/cm$^2$ may also be used for a short period of time.

The compounds of the invention may also be used in cosmetology by reason of their property of stimulating the pigmentation of the skin. The invention therefore provides cosmetic compositions containing an amount of at least one compound according to the invention effective for producing the pigmentation of the skin in association with a vehicle suitable for external application. The vehicles of such compositions are well known to those skilled in the art and do not need to be described in greater detail. For the compounds of the invention vehicles similar to those already proposed for cosmetic compounds containing 5-MOP may be used. The cosmetic compositions of the invention may be in cream, milk, oil or spray form or in all other products for external use. The compounds of the invention may or may not be associated with sun screens or filters in the composition. The amount of the active ingredient employed in the cosmetic compositions of the invention is not critical and may vary according to the intended use thereof. In general, amounts from 0.01 to 0.05% by weight relative to the composition are suitable.

The novel compounds of the invention have a series of properties which make them of particular interest for the treatment of skin afflictions, viz.:

appreciable photoreactivity with nucleic acids, producing an antiproliferatory effect;

absence of induction of cross-linking in the DNA;

induction of only mono-additions in DNA, resulting in the stopping of the synthesis of DNA and RNA;

slight phototoxic effects, thus causing little or no erythema; and a low mutagenic power in contrast to the bifunctional furocoumarins currently used in PUVA therapy which has a considerable mutagenic power.

The following examples, which are given by way of illustration only, show the preparation and properties of the novel compounds of the invention.

EXAMPLE 1

Nitro-3(methyl-2' methoxy-3' phenoxy-1')-4 pyridine, (compound 8a, formula VIII, where R'=CH$_3$ and Y=NO$_2$)

Compound of formula 6, i.e., methyl-2-methoxy-3-phenol (4.35 g, 31.5 mmol) is added to a potassium hydroxide solution (1.76 g) in ethanol (40 ml) and the resulting solution is evaporated dry. The residue is dissolved in dimethylformamide (DMF) (50 ml). The nitro-3-chloro-4 pyridine 7 (5 g, 31.5 mmol) in solution in the DMF (50 ml) is added all at once. The mixture is stirred at ambient temperature for 1 hour then heated to 60° C. for 1 more hour and evaporated dry under reduced pressure. The residue, taken from the water, is extracted with chloroform, washed with water, and the evaporated organic phase provides a residue which is recrystallized in alcohol in the presence of animal charcoal to yield 5 g (61%) of yellow crystals, mp 115°-117° C.

Analysis % calculated for C$_{13}$H$_{12}$N$_2$O$_4$: C 60.00, H 4.6, N 10.7. Found: C 59.8, H 4.6, N 10.7.

EXAMPLE 2

Amino-3[(methyl-2' methoxy-3' phenoxy-1')]-4 pyridine (compound 8b, formula VIII, where R'=CH$_3$ and Y=NH$_2$).

The nitrogenous compound 8 a obtained in example 1 (5 g, 19.2 mmol) is dissolved in absolute ethanol (100 ml) and hydrogenated by stirring in a hydrogen atmosphere in the presence of Raney nickel catalyst (5 g) until the absorption of the theoretical amount of hydrogen. The catalyst is filetered and the evaporation of the ethanol provides a solid which is recrystallized in ethanol, yielding 3.1 g (70%) colorless needles, mp 143° C.

Analysis % calculated for C$_{13}$H$_{14}$N$_2$O$_2$: C 67.8, H 6.0, N 12.1. Found: C 67.6, H 5.9, N 11.9.

EXAMPLE 3

Methyl-6-methoxy-7-pyrido[4,3-b]benzofuran (compound 9a, formula IX, where R'=CH₃, Y'''=CH₃)

The aminopyridine 8b (2.3 g, 10 mmol) obtained from example 2 is stirred at 0° C. and treated with an aqueous solution of sodium nitrite (0.7 g) added drop by drop at a temperature below 0° C. After 15 minutes of stirring at 0° C. the solution of the diazoic derivative 8c thus formed is added drop by drop to a mixture of acetone (50 ml), water (12.5 ml) and cupric chloride (3.3 g) heated to 35°–40° C. and vigorously stirred. After maintaining for 15 minutes for 15 minutes at this temperature, the mixture is heated under reflux for 5 minutes, cooled and alkalinized by adding a sodium hydroxide solution. After extraction with chloroform and washing with water, the residue of evaporation of the solvent is recrystallized in hexane to yield 360 mg (16.9%) colorless needles, mp 141°–143° C.

Analysis % calculated for $C_{13}H_{11}NO_2$: C 73.2, H 5.2, N 6.5. Found: C 72.9, H 5.2, N 6.3.

EXAMPLE 4

Methyl-6-hydroxy-7 pyrido(4,3-b)benzofuran (compound 9b, formula IX where R'=CH₃ and Y''=H).

The compound 9a obtained from example 3 (2.5 g, 11.7 mmol) in the anhydrous pyridinium chloride (25 g) is heated to 220°–230° C. for 15 minutes and the mixture is poured into icy water. The resulting solid is filtered and recrystallized in ethanol to yield 1.8 g (77%) of the hydrochloride of compound 9b, mp>300° C. This hydrochloride is liberated quantitatively by dissolving it in boiling water and treating it with excess ammonia. The compound 9b recrystallizes in toluene into colorless crystals, mp 260°–263° C.

Analysis % calculated for $C_{12}H_9NO_2$: C 72.3, H 4.5, N 7.0. C 72.5, H 4.7, N 7.0.

EXAMPLE 5

Methyl-6-hydroxy-7 formyl-8 pyrido[4,3-b]benzofuran (compound 10a, formula X, where X=O and R'=CH₃)

The mixture comprising the hydroxylated derivative 9b (5 g, 25.1 mmol), hexamethylenetetramine (5.25 g) and acetic acid (75 ml) is heated under reflux for 3 hours. After adding 100 ml of 3N hydrochloric acid, the new mixture is heated under reflux for another 3 hours and the solvent is evaporated. The residue is put back into water, neutralized with a saturated solution of sodium hydrogenocarbonate and the resulting precipitate is filtered and dried, and recrystallized in methanol yielding 2.1 g (36%) yellow needles, mp 212° C., corresponding to the hemihydrate of compound 10a.

Analysis % calculated for $C_{13}H_9NO_3$, $\frac{1}{2}H_2O$: C 66.1, H 4.2, N 5.9. Found: C 65.9, H 4.0, N 5.8.

EXAMPLE 6

Methyl-6 carbethoxy-9 pyrido[3',4';4,5]furo[3,2-g]coumarin (compound 11a, formula XI where R'=CH₃ and Y'''=COOC₂H₅.

The aldehyde 10a (2 g) is heated under reflux in ethanol (10 ml) with diethylmalonate (2.28 g) and piperidine (0.2 ml) for 20 minutes. The cooled reactive mixture provides a solid which recrystallizes in ethanol yielding 2.6 g (91%) yellow needles, mp 256°–258° C.

Analysis % calculated for $C_{18}H_{13}NO_5$: C 66.8, H 4.0, N 4,3. Found: C 66.6, H 4.0, N 3.9.

EXAMPLE 7

Methyl-6-pyrido[3',4';4,5]furo[3,2-g]coumarin (formula I, where R=H and R'=CH₃)

Compound 11a, methyl-6 carbethoxy-9 pyrido[3',4';4,5]furo[3,2-g]coumarin, (2,6 g, 8 mmol) is heated under reflux for 2 hours in a mixture of acetic acid (15.6 ml) and hydrochloric acid (14 ml) and the mixture is cooled. The resulting solid is filtered and dried to yield 2.2 g of the acid compound 11b in the form of a hydrochloride. The latter is dissolved in hot water, alkalinized with ammonia and neutralized by acetic acid. The resulting solid is filtered and dried to yield 1.9 g (80%) of a solid, mp>300° C. This acid (500 mg) mixed with cupric oxide (5 mg) and o-phenanthroline (5 mg) is heated to 200°–220° C. in quinoleine (2.7 ml) for 20 minutes, then for 5 minutes at 240° C. The cooled mixture provides a solid which recrystallizes in toluene yielding 210 mg (49%) of the pure compound mentioned in the heading, mp 295°–302° C.

Analysis % calculated for $C_{15}H_9NO_3$: C 71.7, H 3.6, N 5.5. Found: C 71.7, H 3.7, N 5.3.

EXAMPLE 8

N-methyl O-(dimethyl-4',8' coumarinyloxy)-7 piperidone-4 oxime (compound of formula IV where R=R'=Y=CH₃)

To a mixture of 850 mg (3.92 mmol) of hydroxylamine having the formula

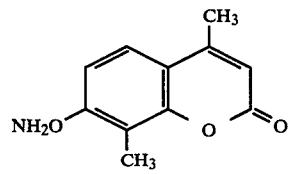

and methyl-1-piperidone-4 hydrochloride in 40 ml of ethanol were slowly added, while stirring, 15 drops of concentrated hydrochloric acid. After several minutes, the mixture starts to dissolve then precipitated. After 3½ hours of stirring the precipitate is centrifugally extracted, washed with alcohol and dried. 1.24 g (3.6 mmol) (84%) of the hydrochloride of the heading compound was obtained (mp 204°–205° C.). Then 300 mg of this hydrochloride in suspension in 6 ml of water were neutralized by a saturated solution of sodium hydrogenocarbonate. After 0.5 hours stirring the precipitate formed is centrifugally extracted, washed with water and dried. After two crystallizations in ethanol, 120 mg of base (mp 138° C. dec) are obtained.

Analysis % calculated for $C_{17}H_{20}N_2O_3$: C 67.98, H 6.71, N 9.33. Found: C 67.65, H 6.73, N 9.27.

EXAMPLE 9

Tetrahydro-1,2,3,4 trimethyl-2,6,10 pyrido[3',4';4,5-]furo[3,2-g]coumarin (compound of formula V where R=R'=CH₃ and Y=CH₃)

2.28 g (6.78 mmol) of the oxime prepared in example 8 are put into suspension in 60 ml of acetic acid containing 7% dry hydrochloric acid. The mixture is heated to 80° C. under a small stream of hydrochloric acid for 5 hours. After cooling, the precipitate formed is centrifugally extracted, washed with acetic acid and dried.

1.600 g (4.54 mmol) (67%) of the hydrochloride of the compound in the heading is obtained (mp 268°–271° C. dec).

1.50 g of this hydrochloride in suspension in 5 ml of water are neutralized by a saturated solution of sodium hydrogenocarbonate. After 0.5 hour of stirring the precipitate which is centrifugally extracted, washed with water, dried and crystallized twice in alcohol, provides 66 mg of base (mp 201°–202° C.).

NMR(CDCl$_3$, δ ppm, 60 MHz), 2.5(3H,s, CH$_3$);2.58(6H,s,CH$_3$); 2.9 (4H, broad s, CH$_2$ in 3 and 4); 3.63(2H,broad s, CH$_2$ in 1); 6.26(1H, m,H$_9$);7.43(1H, s, H$_{11}$).

Analysis % calculated for C$_{17}$H$_{17}$NO$_3$: C 72.06, H 6.05, N 4.94. Found: C 71.85, H 6.05, N 4.91.

EXAMPLE 10

Tetrahydro 1,2,3,4-dimethyl-6,10 pyrido[3′,4′;4:5]furo[3,2-g]coumarin (compound of formula V where R=R′=CH$_3$ and Y=H)

The compound of the heading was prepared, according to the procedure described for the compound of example 9, from hydroxylamine and piperidone-4 hydrochloride.

The oxime intermediate was not characterized. From 1.360 g (6.63 mmol) of hydroxylamine, 1.150 g of raw hydrochloride of the compound of the heading (56.8%) (mp 285°–290° C.) was obtained.

The corresponding free base, recrystallized in alcohol, is in the form of colorless needles (mp 211°–212° C.).

MS m/e 269(M+),240,212

NMR(CDCl$_3$, δ ppm, 60 MHz); 1.73(1H,s,H$_2$);2.43(3H,d,CH$_3$ in 10); 2.53 (3H, s, CH$_3$ in 6); 2.83 (2H, m,CH$_2$ in 3); 3.2(2H, m, CH$_2$ in 4); 3.96(2H, m,CH$_2$ in 1); 6.16(1H, m, H$_9$); 7, 33 (1H, s, H$_{11}$).

Analysis % calculated for C$_{16}$H$_{15}$NO$_3$, ½H$_2$O: C 69.05, H 5.80, N 5.03. Found: C 68.87, H 5.92, N 4.77.

EXAMPLE 11

Dimethyl-6,10 pyrido[3′,4′;4,5]furo[3,2-g]coumarin (compound I where R=CH$_3$ and R′=CH$_3$)

404 mg (1.32 mmol) of the hydrochloride obtained in example 10 are put into suspension in 15 ml of Decaline and heated under reflux in the presence of 300 mg of 10% palladium carbon (Pd/C) for 5 hours. The Pd/C is filtered hot and washed with 5 ml of hot Decaline. After cooling the crystals formed are centrifugally extracted and dried. 130 mg of the compound in the heading are obtained which crystallizes from a mixture of CH$_2$Cl$_2$/EtOH in the form of colorless needles (mp 270°–271° C.) MS m/e 265(M+),237, 18.

NMR (CDCl$_3$,δ ppm, 100 MHz), 2.58(3H, d, J=1,2 Hz, CH$_3$ in 10), 2.67(3H, d, J=0,5 Hz, CH$_3$ in 6); 6,34(1H, d, J=1.2 Hz, H$_9$);7.59 (1H, dxd, J=0.9 Hz, J=5.7 Hz, H$_4$); 8.08 (1H, s, H$_{11}$);8.70(1H, d, J=5.7 Hz, H$_3$); 9.29 (1H,d, J=0.9 Hz, H$_1$).

Analysis % calculated for C$_{16}$H$_{11}$NO$_3$: C 72.44, H 4.18, N 5.28. Found: C 72.13, H 4.25, N 4.71.

EXAMPLE 12

Under the same conditions as example 11 the aromatization of 248 mg (0.77 mmol) of the compound obtained in example 9 provides 109 mg of the crude product. After two recrystallizations in the CH$_2$Cl$_2$/EtOH mixture 77 mg (37%) of the compound of formula I, where R=CH$_3$ and R′=CH$_3$, are obtained.

The novel compounds of the invention have been subjected to tests permitting their activity as cosmetics, medicinals and pharmaceuticals to be appreciated.

In the description which follows the compounds of formula I according to the invention wherein R′ is CH$_3$ and R is H and R′ is CH$_3$ and R is CH$_3$ will be respectively designated by abbreviated references 5a and 5b.

Compounds 5a and 5b and some intermediate derivatives produced in the course of their synthesis (compounds 14a and 14b) have been studied from the standpoint of their photophysical and photochemical properties and their reactivity in vitro in respect to DNA. These studies, first of all, essentially concerned their spectroscopic properties in solution: (1) absorption of radiation and in particular absorption of radiation at 365 nm, i.e., at the wavelength used for most photobiological studies; (2) emission; (3) photochemical stability during ultraviolet radiation (UVA) at doses comparable to those generally used in photobiological experiments. In a second stage, the affinity of these molecules vis-à-vis DNA, then their photoreactivity during irradiation of DNA-pyrido psoralen complexes were tested (DNA fusion-renaturation experiments).

Compound 5b has a coefficient of molecular absorption at 365 nm mardekly less than that of psoralen.

The free molecule of compound 5b in solution has good photochemical stability in respect to UVA radiation. The thermal denaturation-renaturation experiment on DNA modified by this compound in the presence of UVA results in values of the non-renaturated fraction in the vicinity of 100% up to an incident dose of 27 kJ/m$^2$.

The result of these in vitro studies is that the compounds 5a and 5b are capable of forming only monoadditions on DNA.

The monofunctional character of the novel compounds 5a and 5b was again confirmed by the following experiments.

(1) Use of specifically blocked yeast mutants in the repair of crosslinks of the DNA It is known that photoaddition of bifunctional furocoumarins induced both cross-links and monoadditions on the bases of DNA. Monofunctional furocoumarins only produce the latter reaction.

For the experiments use was made of a yeast mutant pso2 which has the following properties: (a) it is much more sensitive than the wild type from which it derives the lethal effect of the photoaddition of bifunctional psoralens. ("Isolation and characterization of pso mutants sensitive to photo-addition of psoralen derivatives in *Saccharomyses cerevisiae*", J. A. P. Henriques and E. Moustacchi, Genetics 95,273–288(1980)) and other cross-linking agents such as bifunctional nitrogenous mustards ("Mutagenesis induced by mono and bifunctional alkylating agents in yeast mutants sensitive to photoaddition of furocoumarins (pso)", O. Cassier and E. Moustacchi, Mutation Res. 84, 37–47(1981)), or mitomycine C. (b) It is relatively insensitive, compared to the wild type, to the photoaddition of monofunctional psoralens of the 3-carbethoxypsoralen type or to monofunctional mustards. Similarly pso2 has the same sensitivity as the wild type to ultraviolet radiation at 254 nm or to ionizing radiation which is known to produce essentially lesions of the strands and breaks in the DNA without producing cross-links in biologically significant doses. (c) It has been biologically demonstrated that the pso2 mutant is blocked in the repair of cross-links in DNA. ("The fate of 8-methoxypsoralens photo-induced cross-links in nuclear and mitochondrial yeast DNA:

Comparison of wild type and repair deficient strains, N. Magana-Schwencke, J. A. P. Henriques. R. Chanet and E. Moustacchi, Proc. Natl. Acad. Sci. (b 1981). This blocking is specific, because the pso2 mutants repair, like the wild type, the monoadditions photo-induced on the DNA.

In other words, if the pso2 mutant is shown to be more sensitive than the wild type of the lethal effect of an agent, it may be deduced that this agent is capable of producing cross-links in the DNA in such a way that it is a bifunctional compound. On the other hand, if the pso2 mutant has the same sensitivity as the wild type to a given agent, it may be concluded that the agent does not cause cross-links and it is therefore a monofunctional type.

The experiments show that the pso2 mutant is 3 to 4 times more sensitive to products 14a and 14b than the isogenic wild strain. The products 14a and 14b are therefore of the bifunctional type.

On the other hand, it has been found that the pso2 mutant has the same sensitivity as the wild type to the photoaddition of product 5b. Since the mutant has the same capacity as the wild type to repair the monoaddition lesions, it is clear that compound 5b is of the monofunctional type. It has also been confirmed on the yeast strains that the novel compounds 5a and 5b are very photoreactive.

(2) Direct biochemical verification of the absence of cross-linking in DNA of cells treated with product 5b and irradiation at 365 nm.

The validity of the foregoing conclusions is confirmed by in vivo biochemical analysis. Indeed, DNA of cells of the wild type were extracted immediately after treatment with product 5b at a concentration of $10^{-5}$M and irradiation with two doses of radiation at 365 nm (30% and 5% survival rate). After separating the nuclear DNA and the mitochondrial DNA by gradient density of cesium chloride, the DNA is broken so as to have segments of homogeneous size (one cross-link on the average permolecule for 8-methoxypsoralen), it is denatured and renatured. If the DNA contains cross-links between the strands it renatures itself and is found in the double chain form separable by gradient density from single chain DNA. On the other hand, when the DNA does not contain any cross-links it remains in single chain form after renaturation. It was the latter situation which was observed experimentally with product 5b. The control experiments with 8-methoxypsoralen carried out under the same conditions show cross-linked double strand DNA. For details of the technique used, see: "The fate of 8-methoxypsoralen photo-induced cross-links in nuclear and mitochondrial yeast DNA:Comparison of wild type and repair-deficient strains, "N. Magana-Schwencke, J. A. P. Henriques, R. Chanet and E. Moustacchi, Proc. Natl. Acad. Sci(USA), (1981) and "Absence de pontage interchaine dans l'ADN triaté par le 3-carbéthoxypsoralène et une irradiation à 365 nm" (Absence of cross-linking between strands of DNA treated with 3-carbethoxypsoralen and irradiation at 365 nm), N. Magana-Schwencke D. Averbeck, J. A. P. Henriques and E. Moustacchi, C.R. Acad. Sci. Paris 291, 207–210(1980).

In sum, the use of the pso2 mutant and the direct examination of the DNA of cells treated in vivo clearly show that product 5b, is indeed of the monofunctional type.

The procedures used to determine the photobiological activity of the novel derivatives of psoralen according to the invention are described in particular in the following references:

D. Averbeck, E. Bisagni, E. Moustacchi, Biochim, Biophys. Acta 518,464(1978);

D. Averback, E. Moustacchi, Mutation Res. 88, 133(1979),

D. Averbeck, E. Moustacchi, Photochem. Photobiol, 31, 475(1980); and

D. Averbeck, S. Averbeck, F. Dall. Acqua, Il Farmaco, 36, 492(1981).

For the detection of the photobiological activity the unicellular eukaryote system of Saccharomyces cerevisiae yeast has proved to be very useful, see D. Averbeck in Trends in Photobiology, Proc. of the 8th International Congress in Photobiology, July 20–25, 1980, Strasbourg, Eds., C. Helene Charlier, Th. Montenay-Garestier, G. Laustriat, Plenum Publishing Corporation, New York, 1981. This photobiological activity has in effect been defined by the induction of lethal effects, the induction of "small colony" cytoplasmic mutations (damage in the mitochondrial DNA) and the induction of nuclear mutations (reverse and forward). The experiments were conducted in the customary manner used and described in the above articles.

In the trials on the induction of lethal effects in yeast expressed by the induction of the capacity of the cells to form a colony, it was observed that in presence of radiations at 365 nm(UVA) the compound 14a of example 9 and compound 14b of example 10 having equimolar concentrations ($5 \times 10^{-5}$M) manifest an activity comparable to that of 8-MOP, a bifunctional agent widely used in PUVA therapy. As a function of the dose of UVA and the survivors, these compounds also show, as regards the induction of cytoplasmic mutations, an activity comparable to that of 8-MOP, therefore a similar photoreactivity with DNA and a bifunctional type of activity.

Compounds 5a and 5b, viz., the compounds of examples 7 and 11(12), have been established to be monofunctional type agents, and their antiproliferatory photoinduced activity, is of great interest, the antiproliferatory photoinduced activity of compound 5a being similar to that of bifunctional 8-MOP and the antiproliferatory photoinduced activity of compound 5b being similar to that of carbethoxy-3 psoralen (3 CPs).

Contrary to 8-MOP, the two compounds have per UVA dose an elevated induction power of "small-colony" cytoplasmic mutations, indicating a considerable photoaffinity for the DNA. As a function of the survivors this induction effectiveness is comparable to that of 3-CPs which is in agreement with the notion of monofunctionality.

It is important to note that for the induction of reverse nuclear mutations (his+) and forward nuclear mutations (can$^R$) as a function of the UVA dose, the compound of example 7 is much less mutagenic than bifunctional furocoumarins(8-methoxypsoralen,5-methoxypsoralen and 4,5',8-trimethylpsoralen) customarily used in photochemical therapy. As a function of the number of survivors which provides an evaluation of the relative effectiveness of the compounds on the induction of mutations, the compounds according to the invention are markedly less mutagenic than 8-MOP but is of an effectiveness comparable to that of 3-CPs.

The fact that the compound, formula XI in example 6, has been established to be completely inactive in the various photobiological tests under customarily used ranges of doses and experimental conditions, shows that the carbethoxygroup in position 3 cancels the induction of photoadditions to the DNA and the photosensitizer effect of the compounds described.

The clinical and therapeutical activity of the compound 5b has been measured on human skin.

10 mg of compound 5b was diluted in 2 g of purified lanolin commercially available under the name ROC hydrocerine which was made fluid by heating to 60° C.

This topical preparation was tested on a round surface 3 cm in diameter at the center of a lombar psoriatic plaque. The amount of product 5b applied was about 30 μg/cm². It was applied two hours before irradiation (UVA) to insure sufficient cutaneous penetration. After these two hours the dose of irradiation was first 5J/cm² and the treatments were repeated Mondays, Wednesday and Fridays until a therapeutic effect appeared. As of the seventh treatment (total dose of irradiation 35 J/cm²) a whitening was observed. Concurrently pigmentation appeared.

No erythema appeared with product 5b. The control zone treated with only lanolin showed no improvement or pigmentation.

In conclusion, the monofunctional products 5a and 5b have photobiological properties which are very favorable for use in photochemical therapy owing to their good antiproliferatory effect which is not accompanied with substantial mutagenic risks. The tests conducted on human skin show these compounds have antipsoriatic and pigmentogenic activity.

What we claim is:

1. Pyrido (3,4-h) psoralens or pyrido (3,4':4,5)furo (3,2-g) courmarins having the formula I

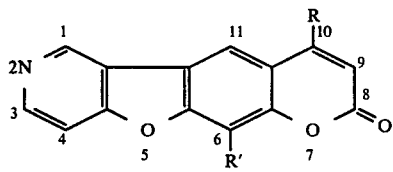

wherein R is selected from the group consisting of a hydrogen atom and a lower alkyl group having from 1 to 4 carbon atoms and R' is selected from the group consisting of a methyl group and a methoxy group.

2. Pyrido (3,4-h)psoralens or pyrido (3',4':4,5)furo (3,2-g) coumarins of claim 1, wherein R is selected from the group consisting of a methyl group and a hydrogen atom.

3. Pyrido (3,4-h) psoralens or pyrido (3',4':4,5)furo (3,2-g) coumarins of claim 1, wherein R' is a methyl group.

4. Pyrido (3,4-h)psoralens or pyrido (3',4':4,5)furo (3,2-g) coumarins of claim 2, wherein R' is a methyl group.

5. Pyrido (3,4-h) psoralens or pyrido (3',4':4,5)furo(3,2-g) coumarins of claim 1, wherein R is a hydrogen atom and R' is a methyl group.

6. Pyrido (3,4-h) psoralens or pyrido (3',4':4,5)furo (3,2-g) coumarins of claim 1, wherein R and R' are both methyl groups.

7. A pharmaceutical composition useful for treating inflammatory dermatoses or for stimulating the pigmentation of the skin, comprising
   an amount of pyrido (3,4-h) psoralens or pyrido (3',4';4,5) furo (3,2-g) coumarins having the formula

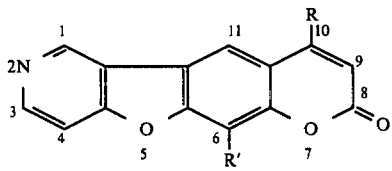

wherein R is selected from the group consisting of a hydrogen atom and a lower alkyl group having from 1 to 4 carbon atoms and R' is selected from the group constisting of a methyl group and a methoxy group; and
   a pharmaceutically acceptable vehicle for local or oral administration.

8. The pharmaceutical composition of claim 7, in a form selected from the group consisting of an ointment and a solution.

9. The pharmaceutical composition of claim 7, wherein said active ingredient is present in a therapeutically effective amount from about 0.1% to about 2% by weight of the pharmaceutical composition.

10. The pharmaceutical composition of claim 9, wherein said active ingredient is present in an amount from about 0.5% to about 2% by weight of the pharmaceutical composition.

11. A method of treating inflammatory dermatoses comprising administering to a patient afflicted with said condition an anti-antiflammatory dermatoses effective amount of the compound of claim 1, or a combination thereof, in combination with irradiation with light in the near ultraviolet range (UVA).

12. The method of claim 11, wherein the inflammatory dermatosis is psoriasis.

* * * * *